(12) United States Patent
Myllymäki

(10) Patent No.: US 6,348,867 B1
(45) Date of Patent: Feb. 19, 2002

(54) CONTROL SYSTEM FOR BUILDING AUTOMATION CONTROLLED BY HUMAN PHYSIOLOGICAL SIGNALS

(75) Inventor: Matti Myllymäki, Espoo (FI)

(73) Assignee: IST International Security Technology Oy, Helsinki (FI)

( * ) Notice: Subject to any disclaimer, the term of this patent is extended or adjusted under 35 U.S.C. 154(b) by 0 days.

(21) Appl. No.: 09/647,959

(22) PCT Filed: Apr. 9, 1999

(86) PCT No.: PCT/FI99/00299

§ 371 Date: Nov. 6, 2000

§ 102(e) Date: Nov. 6, 2000

(87) PCT Pub. No.: WO99/56262

PCT Pub. Date: Nov. 4, 1999

(30) Foreign Application Priority Data

Apr. 9, 1998 (FI) .................................................. 980819

(51) Int. Cl.$^7$ ............................................. G08B 23/00
(52) U.S. Cl. .................... 340/573.1; 340/506; 340/539; 340/825.06
(58) Field of Search ............................. 340/573.1, 539, 340/506, 573.4, 825.06, 825.32, 286.07, 825.49

(56) References Cited

U.S. PATENT DOCUMENTS

| | | | | |
|---|---|---|---|---|
| 4,319,228 A | * | 3/1982 | Daniels ....................... 340/521 |
| 4,952,928 A | * | 8/1990 | Carroll et al. .......... 340/825.54 |
| 5,204,670 A | | 4/1993 | Stinton ................... 340/825.54 |
| 5,228,449 A | * | 7/1993 | Christ et al. ................. 128/691 |
| 5,410,739 A | | 4/1995 | Hart .............................. 455/66 |
| 5,515,858 A | * | 5/1996 | Myllymaki .................. 128/670 |
| 5,568,126 A | | 10/1996 | Andersen et al. ............ 340/574 |
| 5,692,215 A | | 11/1997 | Kutzik et al. ................ 395/838 |
| 5,905,436 A | * | 5/1999 | Dwight et al. ........... 340/573.1 |
| 6,084,516 A | * | 7/2000 | Yasushi et al. .......... 340/573.1 |

FOREIGN PATENT DOCUMENTS

| | | |
|---|---|---|
| GB | 2 150 725 A | 7/1985 |
| GB | 2 312 309 A | 10/1997 |

* cited by examiner

Primary Examiner—Daniel J. Wu
Assistant Examiner—Phung Nguyen
(74) Attorney, Agent, or Firm—Weingarten, Schurgin, Gagnebin & Lebovici LLP

(57) ABSTRACT

An automatic control system for actuators and security devices in building automation. A wrist-held sensor and transmitter unit (11) transmits repeatedly, in the form of short telegrams, messages indicating the physiological condition of user to a receiver and control apparatus (12), which is placed in a monitored space either as a separate unit or a part of an appliance to be controlled. The receiver and control apparatus (12), or an information analyzer in data transfer communication therewith, uses the physiological condition of a user as a basis to conduct control selections and to control automatically the actuators and security devices in accordance with the physiological condition of a person who carries the transmitter unit (11). If necessary, the control selections can be influenced also by a piece of information indicating the location of a user. In addition to the automatic control of nearby equipment, the system is also applicable to monitoring the health of a user and to setting off alarms.

7 Claims, 3 Drawing Sheets

CONTROL SYSTEM FOR BUILDING AUTOMATION CONTROLLED BY HUMAN PHYSIOLOGICAL SIGNALS

Figure 1:
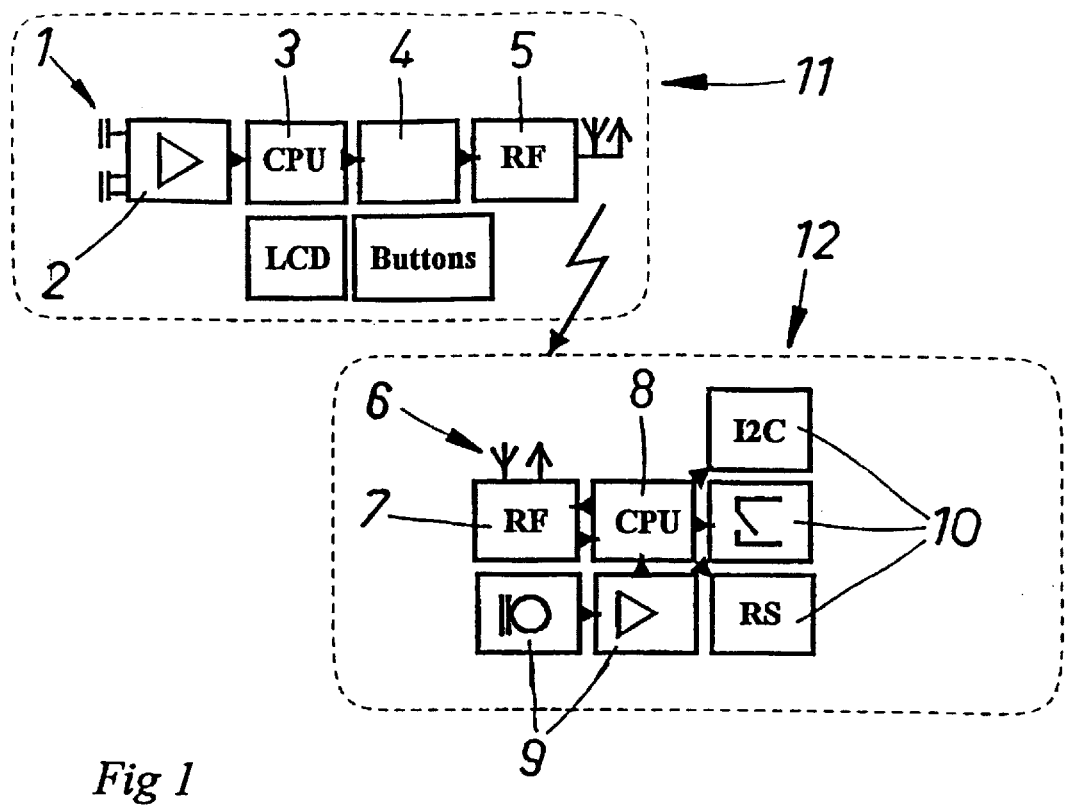

The present invention relates to a control and security system for building automation controlled by human physiological signals, comprising one or more transmitter units, "Wrist nurses", and one or more receivers as well as a central unit. The receivers and the central unit are provided with sensors, processors along with software for processing received information, and control outputs as well as necessary communication links to the appliances being controlled.

Traditionally, the control of HPAE (Heating, Plumbing, Air conditioning, Electricity) equipment in buildings, such as homes and offices, is performed by monitoring the status of the environment as well as according to parameters programmed by a user for the control unit. The control is intended for monitoring human needs as effectively as possible. The security systems are also intended for creating an environment as safe as possible in accordance with human needs. Traditionally, the control of personal clearance, property, and health security systems is performed by means of a control keyboard and/or control switches under the self-acting control of a user. Personal clearance is generally carried out by using separate equipment and various clearance passes or cordless transmitters activated by external control. In property-related security systems, a keyboard is used e.g. for switching a burglar surveillance on and off. In health security systems, a control switch is used for controlling e.g. a passivity surveillance by means of a home/away switch. Referring especially to children and the elderly, the above control systems are too sophisticated and cause unnecessary alarms and restrict the use of security equipment. Also, false alarms in alarm systems are most commonly caused by operating errors, regarding both automobile alarms and buildings. In addition, security systems for a building and an automobile require their own operating equipment of the above type. In personal clearance equipment, the service is generally limited to controlling clearance passes as well as to monitoring working hours, but also these require a self-acting control by the user.

In general, separate systems have their own operating and control equipment, even if certain actions were linked together electrically for carrying out a joint operation. For example, the activation of burglar surveillance may shut down service water and drop room temperatures. What is typical is that all traditional systems require control actions from a user every time the requirements differ from set parameters, or if it is desirable to switch some function on or off. Attempts have been made to relieve the situation by means of so-called smart house solutions, wherein the intention is to make the equipment control as easy as possible. Nevertheless, such systems are too difficult to operate e.g. for children and the elderly, resulting in false alarms caused by operating errors as well as in dissatisfaction with the operation of equipment.

An object of the invention is to provide a control system for building automation, wherein the control is based on the location of people present in a space as well as the physiological condition thereof and the fact that a common control device is used for controlling the user terminals of all sub-systems either directly or through a local network (Lon, Instabus, etc.) automatically without a self-acting control by the user. The feedback for users, regarding automatically effected control functions, can also be delivered as voice messages.

This object is achieved on the basis of the characterizing features set forth in the appended claim 1.

Another novelty in the control system is that the users are able to control all pieces of equipment by means of a single wrist-held monitor device, which also enables the monitoring and surveillance of health condition both in and out of a building. When connected to a mobile phone, it provides a portable security system.

Also new is that the system enables e.g. an automatic switch-on and -off action of lights depending on where a person is moving, even in such a manner that, when going to bed, the system recognizes on the basis of physiological signals that the location is used for sleeping and switches off the ceiling light automatically. In other words, it is possible for the system to learn a condition in which a person is resting in order to switch off the light in this condition, and another condition which implies active working in order not to switch off the lights even in nighttime. In similar fashion, the outdoor and indoor lights of a building can be switched on automatically in the dark as the user approaches his or her home.

Likewise, the air conditioning/heating of a space is controlled in accordance with the physiological condition of a person, e.g. if a person is perspiring, the temperature will be lowered and, respectively, raised if a person is feeling cold. Thus, the heating is controlled according to any given physiological need of a person, in real time and even per room, if so desired.

Furthermore, when knowing the location of a person in a space, it is possible to direct e.g. phone calls to where the person is at a given time. The position information can also be transmitted to a telephone operator for directing the paging precisely to where a sought-after person is moving. The control of entertainment equipment can also be implemented in such a manner that, as the user is moving from room to room, the TV or radio program that the user is following is switched on in the space he or she is entering.

By means of positioning, it is possible to achieve in personal clearance an automatic control for locking in such a manner that, as the user is coming home or moving about in an office, the door can be unlocked automatically as he or she approaches it.

The monitoring of personal clearance and working hours can also be accompanied, in addition to working hours, by information about where the user has spent his or her working hours (e.g. in conference room/own office), as well as by information about a cumulative alertness status/ activity level. The control system's infra and sound sensors, together with positioning, provide a perimeter protection in such a way that it allows the user to open a door or a window, but when done by an outsider, such opening triggers an alarm.

It is also novel that the above qualities provide for an elderly person, a demented person, and physically or mentally handicapped people an automatically controlled environment managing system, which is additionally able to learn the most important daily chores and seeks to anticipate the needs of a user. By virtue of positioning, the user can be reminded of matters relating to daily chores, like he or she can be reminded of adequate clothing when going out, or eating or taking medication when coming to kitchen. It is also possible to preheat an automobile at a usual departure time in winter.

The invention creates a whole new concept for the term smart house as the users are capable of controlling their environment through their own physiological signals.

Figure 2:
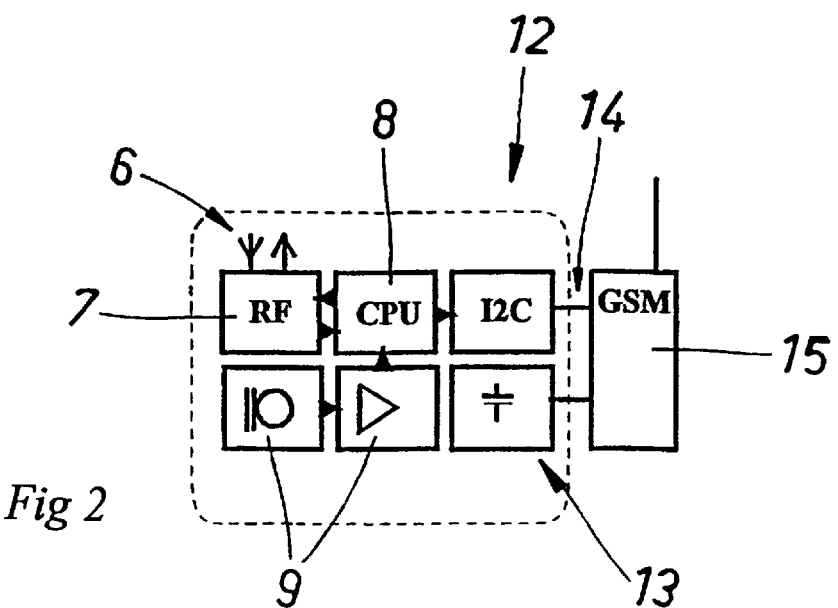
Figure 3:
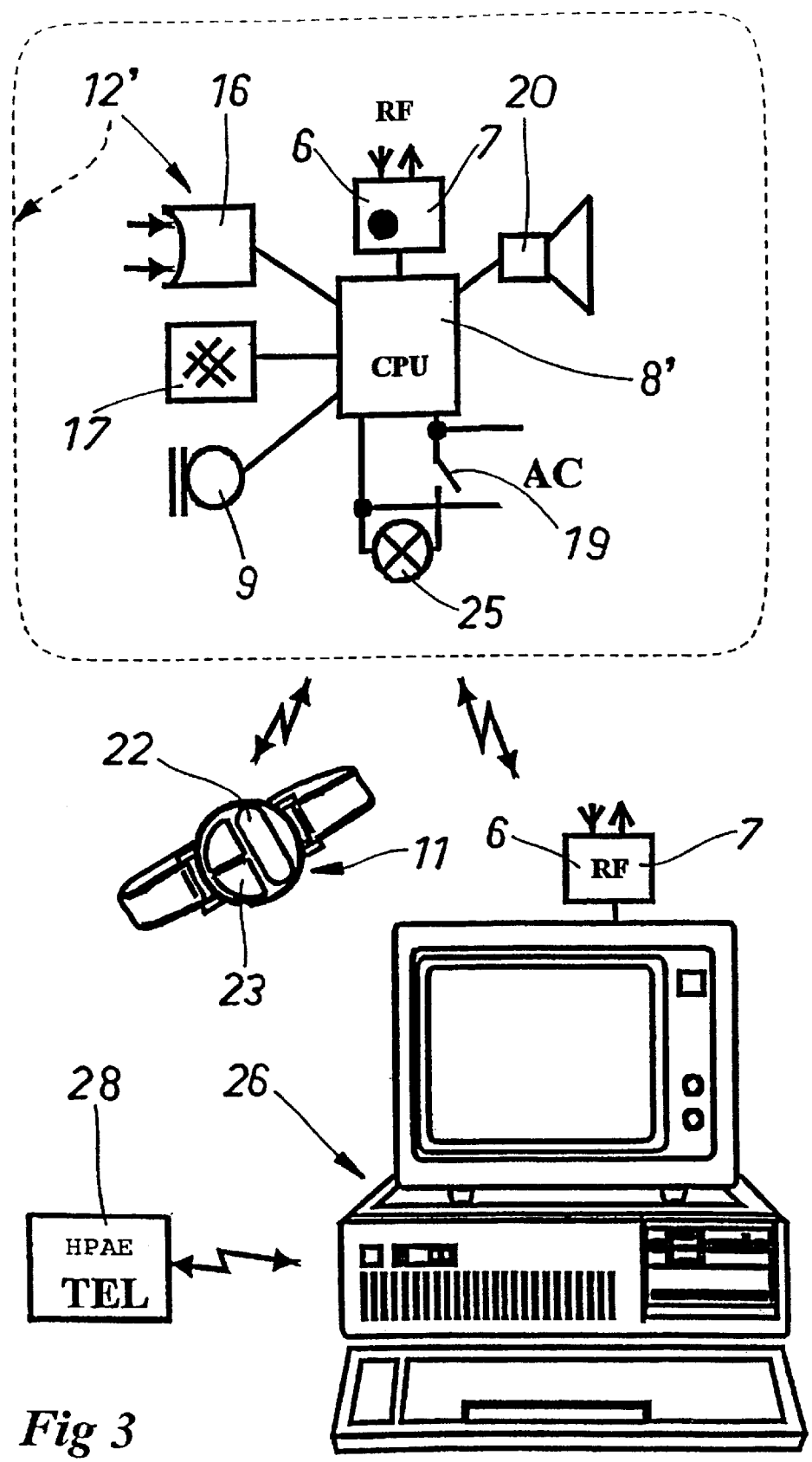
Figure 4:
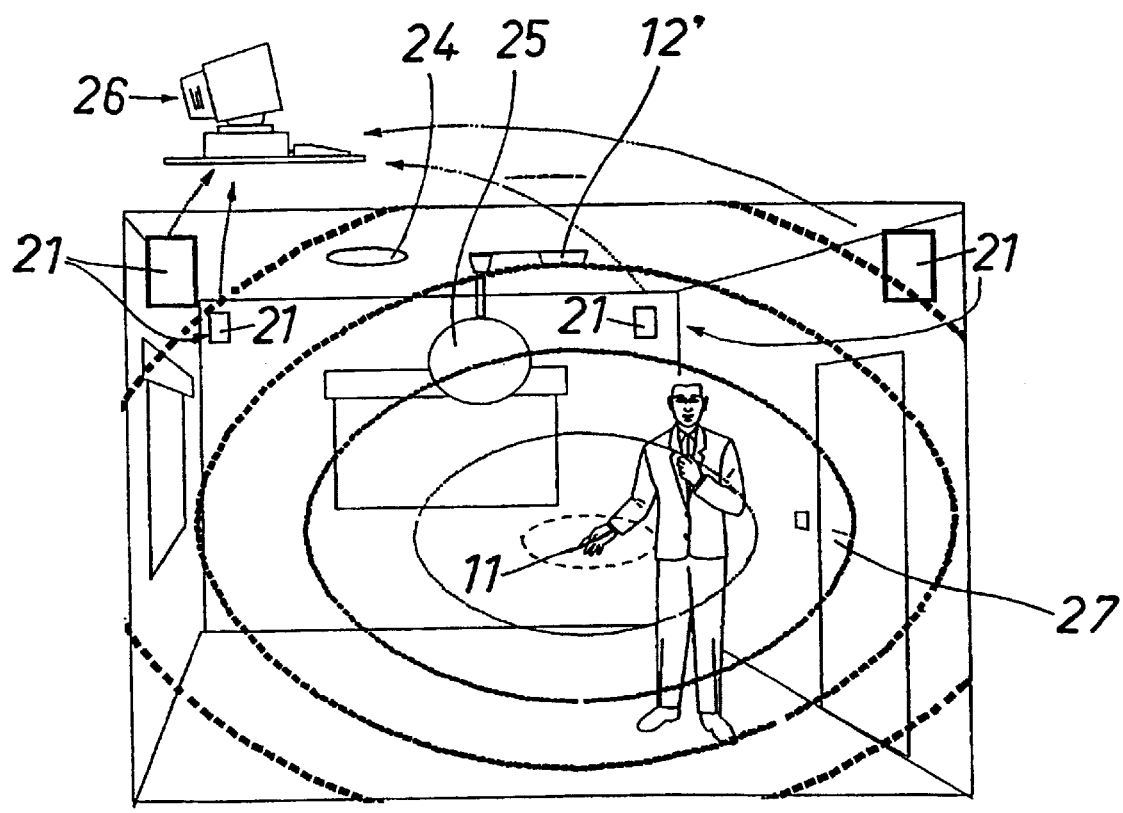

The invention will now be described in more detail with reference made to the accompanying drawings, in which FIG. 1 shows basic units 11, 12 for a control system of the invention in a block diagram;

FIG. 2 shows how the simplest receiver and control equipment included in the apparatus is connected to a mobile telephone system;

FIG. 3 shows how a multi-function receiver 12'/6 and a relaying unit 8'/19 as well as a PC-based cental unit 26 included in the apparatus are connected to an HPAE system; and FIG. 4 shows a function for positioning a user 11 or an alarm source 24.

The system of the invention is first described in terms of its structure and operation with reference to FIG. 1. A sensor and transmitter unit 11 is a portable unit carried by a user, which can be held in the user's wrist or elsewhere in body contact. A receiver and control assembly 12 can be a separate unit or an apparatus integrated in a controllable actuator or safety device. Examples of such units have been described in the Applicant's patent applications WO 93/16636 (A 61B 5/11) and WO 95/07652 (A 61B 5/0245). The wrist unit 11 is provided with an alarm button 1 and a number of sensors 2 in skin contact with a user (for the sake of simplicity, the figure only shows one sensor 2). The unit 11 is typically provided with the following sensors: a contact sensor, which indicates whether the device is in operation, a sensor measuring conductivity of the skin, which indicates whether the skin is dry or moist, a heart rate sensor, which indicates the strength of heartbeat and/or heart rate, and a motion sensor (e.g. an acceleration sensor), which indicates the motion activity of a user. On the basis of information provided by these sensors, a microprocessor 3 is capable of making conclusions regarding the alertness status of a user: asleep, awake but passive, moving actively, etc. On the basis of the sensor information, the microprocessor is also capable of making conclusions regarding the physical condition of a user, e.g. based on whether the heart rate is in accord with information indicating the alertness status of the user. The information regarding the alertness and health condition is delivered by way of a concealing unit 4 to a radio transmitter 5, which transmits this information repeatedly in the form of short telegrams to the receiver and control apparatus 12.

The receiver and control apparatus 12 includes a radio receiver 6, a transmitter 7, an infrasound detector 9, a microprocessor 8, and various terminals for a plurality of control outputs 10. The control outputs 10 are used to forward control messages to various communication and alarm systems. It is possible to program a number of wrist units 11 in a single receiver and control apparatus 12 for establishing a multiple-user control system. The processor 8 can be provided with a variety of programs for a variety of applications. In terms of its operation, the receiver and control apparatus 12 included in the control system is based on messages transmitted by the wrist-held sensor and transmitter unit 11 and concealed by using per se known methods, e.g. encrypting 4 as well as a device-specific ID code. A transmission gap between the messages is controlled by changes in the physiological status of a user. Thus, the messages have a low risk of collision. For examples, as the motion activity increases, the transmission rate of messages increases as well. By means of the above-mentioned messages, the wrist unit or the sensor and transmitter unit 11 of the control system informs the receiver and control apparatus or unit 12 about the physiological condition and the presence of a user. The infrasound detector 9 detects a low-frequency sound produced by opening a door. The processor 8 is provided with software which uses the detector 9 to detect the opening of a building or automobile door and to compile, along with messages from the wrist unit 11, information as to whether the user is going out or coming in through the doorway. The wrist unit 12 has its contact sensor 2 to reveal whether the device is fitted around the user's wrist. Thus, taking it off the wrist switches the wrist unit 11 to a low-current state and the information is transmitted to the receiver 6 and, thus, can also be used as an alarm message.

For example, when the user steps out of an apartment or automobile, a message about the opening of a door is received from the infrasound detector 9 while the wrist unit 11 is simultaneously transmitting telegrams. When the telegrams run out as the user is leaving the operating range of the wrist unit, the microprocessor 8 has its software revealing that the user has left the monitored space.

Following the above, the software of the processor 8 switches on burglar surveillance and/or transmits to the personal clearance system a message about the exit of a user by effecting the data transfer either by a radio frequency or fixed terminal 10. The discussed function can also be used in safety systems for the elderly as a time-dependent personal clearance for a demented person, which allows free daily movement but produces an alarm e.g. in nighttime, if the user leaves the monitored space.

When the user and the wrist unit 11 enter a monitored target area, the control apparatus 12 identifies an accepted ID and, if necessary, the opening of a door as well as switches off burglar surveillance and/or transmits a notification about the presence to a personal clearance or outpatient alarm centre 10. After this, the physiological signals transmitted by the wrist unit 11 control the required heating and ventilation as per target area.

FIG. 2 depicts an application of the invention, wherein the novel control system in connection with a mobile phone system provides, along with a wrist unit 11, a portable security system. The control system can be set in connection with the battery casing of a mobile phone 15 in such a way that the linkage is established by using terminal points 14 of batteries 13, the control system having its processor simulate the follow-up memory or temperature sensor of a battery as well as forward alarm messages to the software of a mobile phone in a desired form. The linkage can also be made by using a standard mobile telephone connection, the control unit being attached to the base of the mobile phone 15. In the case of a small cellular network, the wrist unit itself may communicate directly with a base station. The automatic control system connected with the mobile phone 15 can also be used for delivering automobile burglary and other such alarms, as well as messages required by a real-time monitoring of the linkage through a cellular phone network to a control facility.

When using an automatic control system of the invention in home, automobile, and office security systems as well as in connection with a mobile phone, it is possible to obtain an integrity whose automatic control can be effected by means of a single wrist unit 11. The system operates in such a way that the automatic control functions of the invention switch automatically a burglar surveillance on and off in various target areas as the user moves from one target area to another and, if necessary, deliver a message about current whereabouts of the user and, if necessary, the physiological signals in association with an automatic alarm of the wrist unit 11 can be delivered to an alarm centre by using e.g. the short communication messages or direct connection of a GSM telephone to a base station.

As shown in FIG. 3, the multi-function receiver 12'/6 can be fitted in connection with a ceiling light fixture 25, whereby a lighting control 19 and a paging function 20 as well as a power supply for the appliance are easily implemented. Likewise, a motion detector 16, a smoke detector 17 can be linked to the same unit, as well as a two-way communication 6, 7, by using prior known infrared and radio-frequency data transfer technology. The connection to a PC serving as a central unit 26 can be established either by a radio-frequency link 6, 7 or a local network 11. The two-way data transfer is used for transmitting health information from the wrist unit 11 to a PC, in which such information is analyzed and sent back to a display 22 of the wrist unit 11 for the user. The two-way link can also be used e.g. for displaying the caller of an incoming phone call or even for controlling nearby appliances, the menu of a relevant state being transmitted to the wrist unit 11 whose selector buttons 23 are used for manually switching e.g. lights on or off etc. The apartment can be provided with a number of multifunction receivers 12'/6 in connection with the light fixtures 25, whereby it is possible to implement openings of doors and windows occurring automatically as the user of the wrist unit 11 is moving (or to be performed by manual control) as well as to implement a localization of various smoke detectors. A localization of the wrist unit 11 is effected by using conventional radio tracking technology, a localization of doors and windows is carried out by using a measurement for the signal strength of infrasounds, such that each multi-function alarm 12' transmits the signal strength measured thereby to the PC 26 whose software calculates on the basis thereof the location of a sound source 11.

FIG. 4 illustrates the components for a tracking system associated with the control system disposed in a single room. The tracking or localization operates in such a way that the wrist unit 11 transmits continuously physiological measuring signals from its user, which are received by tracking receivers 21 for measuring either the phase of a radio signal and/or the signal strength and for transmitting the information to the micro-computer 26 for an analysis. The microcomputer 26 uses the signal strength as a basis for calculating which door or window the sound came from. On the basis of received information, the microcomputer 26 is able to check whether a door was opened by the user of the wrist unit 11 or by somebody else. If the system is set in a surveillance mode and a door is opened by someone other than the user of the wrist unit 11, an alarm is set off. The corresponding equipment can be arranged in a larger apartment as well by placing the tracking receivers 21 in the extreme corners of the apartment or by using the multifunction receivers 12' linked in connection with the light fixtures 25 of the rooms furthest away from each other.

It is essential for a control system of the invention that a receiver or control apparatus 12, 12' or an information analyzer 26 in data transfer communication therewith is capable of performing selections between various control functions on the basis of the physiological condition of a user, the control of actuators and safety devices 12', 28 occurring automatically in accordance with the physiological condition of a person who carries the transmitter unit 11. This system will be particularly beneficial and versatile by virtue of the fact that the control can also be based on a combination of information indicating the alertness and health condition of a user and a piece of information indicating the location of a user.

What is claimed is:

1. An automatic control system for actuators and security devices relating to building automation, including HPAE (Heating, Plumbing, Air conditioning, Electricity) systems in homes and offices, comprising a portable sensor and transmitter unit and a receiver and control apparatus, which is placed in a monitored space as a separate unit or as a part of an appliance to be controlled and which comprises a receiver for the signals of the sensor and transmitter unit, a processor for processing information contained in the received signals, and control outputs for controlling actuators and security devices and, if necessary, for setting off alarms, characterized in that the sensor and transmitter unit is provided with measuring sensors for monitoring the physiological condition of a user, that said signals contain information about the physiological condition of a user, on the basis of which the receiver and control apparatus or an information analyzer in data transfer communication therewith performs continuously or at short intervals repeatedly and automatically control selections on the basis of the physiological condition of a user and, thus, performs actively the on-line control of said actuators and security devices in accordance with the physiological condition of a person who carries the sensor and transmitter unit.

2. A control system as set forth in claim 1, characterized in that the receiver and control apparatus includes a number of receivers disposed in various parts of a monitored space to receive simultaneously a signal from the sensor and transmitter unit, and that, by comparing the signal strengths of various receivers, the receiver and control apparatus is adapted to track down a user, and that the control of the actuators and security devices and the transmission of possible alarms are based on a combination of information indicating the state of alertness or health of a user and a piece of information indicating the location of a user.

3. A control system as set forth in claim 1, characterized in that the sensor and transmitter unit comprises a wrist-held unit and the receiver and control apparatus is integrated as a part of a burglar alarm and smoke detector unit, including a motion detector, a smoke detector, and an infrasound detector.

4. A control system as set forth in claim 1, characterized in that the sensor and transmitter unit transmits a signal indicating the physiological condition of a user as short messages repeated at short intervals.

5. A control system as set forth in claim 1, characterized in that, regarding the automatically performed control functions, the user is given a feedback therefrom in the form of voice messages.

6. A control system as set forth in claim 1, characterized in that the gap between transmissions of messages indicating a physiological condition and transmitted in a wireless fashion by way of radio is controlled on the basis of changes occurring in the physiological condition of a user.

7. A control system as set forth in claim 2, characterized in that:

the sensor and transmitter unit comprises a wrist-held unit and the receiver and control apparatus is integrated as a part of a burglar alarm and smoke detector unit, including a motion detector, a smoke detector, and an infrasound detector;

the sensor and transmitter unit transmits a signal indicating the physiological condition of a user as short messages repeated at short intervals;

regarding the automatically performed controlled functions, the user is given a feedback therefrom in the form of voice messages; and the gap between transmissions of messages indicating a physiological condition and transmitted in a wireless fashion by way of radio is controlled on the basis of changes occurring in the physiological condition of a user.

* * * * *